US008635899B2

(12) United States Patent
Bailey

(10) Patent No.: US 8,635,899 B2
(45) Date of Patent: Jan. 28, 2014

(54) FLAME SAFETY SYSTEM FOR IN SITU PROCESS ANALYZER

(75) Inventor: Edward J. Bailey, Northfield, OH (US)

(73) Assignee: Rosemount Analytical Inc., Solon, OH (US)

( * ) Notice: Subject to any disclaimer, the term of this patent is extended or adjusted under 35 U.S.C. 154(b) by 939 days.

(21) Appl. No.: 12/503,275

(22) Filed: Jul. 15, 2009

(65) Prior Publication Data

US 2011/0012040 A1    Jan. 20, 2011

(51) Int. Cl.
    G01N 7/00    (2006.01)
(52) U.S. Cl.
    USPC ........................................ 73/23.31
(58) Field of Classification Search
    USPC ................................. 73/23.2, 23.31
    See application file for complete search history.

(56) References Cited

U.S. PATENT DOCUMENTS

| 4,135,382 | A | * | 1/1979 | Capone ........................ 73/31.05 |
| 5,318,752 | A | | 6/1994 | Visser .............................. 422/83 |
| 6,120,664 | A | | 9/2000 | Patel et al. ..................... 204/428 |
| 2002/0182552 | A1 | | 12/2002 | Nielsen et al. .................. 431/77 |
| 2004/0182133 | A1 | | 9/2004 | Staphanos et al. ........... 73/23.31 |

FOREIGN PATENT DOCUMENTS

| JP | 62-008107 | 1/1987 |
| JP | 05-226962 | 9/1993 |
| JP | 2004-366143 | 12/2003 |
| JP | 2007-084559 | 3/2007 |

OTHER PUBLICATIONS

Shuk et al., "Zirconia Oxygen Sensor for the Process Application: State-of-the-Art", Sensor & Transducers Journal, vol. 90, Special Issue, Apr. 2008 by IFSA, www.sensorsportal.com.
"X-STREAM $O_2$ Combustion Flue Gas Transmitter", Rosemount Analytical Instruction Manual, Jan. 2009, www.raihome.com.
International Search Report and the Written Opinion for the related International patent application No. PCT/US2010/041809 dated Jul. 31, 2012.
First Official Action dated Jun. 18, 2013 in related Chinese patent application Serial No. 201080012862.6.
CN Publication 101329110A dated Dec. 24, 2008 for application Serial No. 200810141609.5. With English Abstract Only.
JPO Office Action and Translation for the related International patent application No. 2012-520714, dated Jul. 30, 2013. 18 pages.

* cited by examiner

Primary Examiner — Daniel S Larkin
Assistant Examiner — Jamar Ray
(74) Attorney, Agent, or Firm — Kelly, Holt & Christenson

(57) ABSTRACT

A method of operating a process a combustion analyzer having a measurement cell is provided. The method includes exposing the measurement cell to exhaust of a combustion process where fuel and oxygen are combined in a burner to produce a flame. The measurement cell is heated to a temperature above a flashpoint of the fuel. When a condition is detected, such as a fault or abnormal situation, gas is directed to the measurement cell to form a gaseous barrier between the measurement cell and unburned fuel while the detected condition exists. Once the condition abates, the gas flow is disengaged and process combustion gas measurements are provided.

4 Claims, 5 Drawing Sheets

FLAME SAFETY SYSTEM FOR IN SITU PROCESS ANALYZER

BACKGROUND

Industrial process industries primarily rely upon energy sources that include one or more combustion processes. Such combustion processes include operation of a furnace or boiler to generate energy from combustion, which is then used for the process. While combustion provides relatively low-cost energy, its use is typically regulated and combustion efficiency is sought to be maximized. Accordingly, one goal of the process management industry is to reduce the production of greenhouse gases by maximizing combustion efficiency of existing furnaces and boilers.

In situ or in-process analyzers are commonly used for the monitoring, optimization, and control of combustion processes. Typically, these analyzers employ sensors that are heated to relatively high temperatures and are operated directly above, or near, the furnace or boiler combustion zone. Known analyzers, such as that sold under the trade designation X-Stream $O_2$ Combustion Flue Gas Transmitter available from Rosemount Analytical Inc. of Solon, Ohio (an Emerson Process Management company), often employ zirconia oxide sensors heated to a temperature above approximately 700° Celsius (1300° Fahrenheit). If the combustion process should suffer a flame out condition, raw fuel and air could be exposed to this sensor which, by virtue of its elevated temperature, could become an ignition source with the possibility of precipitating an explosion.

Known analyzers generally employ a sintered metal or other diffuser positioned between a measurement cell and the process combustion gas to allow the process gas to diffuse to the measurement zone while minimizing flow effects and reducing measurement cell contamination. The diffuser readily allows the process gas to contact the heated measurement cell itself and, in the case of the process combustion gas is replaced by a flammable gas, enables an explosion. This situation can occur if the combustion flame is extinguished and fuel continues to flow.

Some process analyzers are approved for hazardous area operation. Some approvals include those provided by the Canadian Standards Association (CSA), Factory Mutual (FM), ATmosphares EXplosibles (ATEX), et cetera. Typically, hazardous area-approved analyzers include a flame arrestor that is added over the diffuser with the intent of quenching, or otherwise inhibiting, an explosion that might occur in front of the heated measurement cell, thereby preventing the ignition of the larger fuel volume in the boiler or combustion zone. These flame arrestors have been tested and approved in the past. However, it is believed that the safety provided by such arrestors can be improved. Moreover, the utilization of the flame arrestors may inhibit, to some degree, access to the measurement cell thereby increasing measurement lag.

State of the art process safety systems generally provide a flame scanner to alert an operator and/or send an electrical signal indicating that the flame is extinguished and that raw fuel may be flowing. Fully automated systems immediately shut down fuel flow, while manual systems generally require operator intervention.

A potentially hazardous situation can also arise during the initial lighting of the process burner or boiler, where fuel is introduced and an ignition source is used to initiate a flame. In some situations, raw fuel may reach the oxygen sensor (heated by its own heater to a temperature of 700° Celsius) which may provide a source of ignition prior to the intended ignition source. This can cause a potential flash or explosion. Typically, either a flame arrestor is used on the oxygen sensor or the analyzer is not powered during boiler or furnace startup. The non-powered analyzer is completely safe since the oxygen sensor is not heated and thus cannot form an unintended source of ignition. However, since the analyzer is non-functional for 30-45 minutes after startup, the analyzer is unavailable during the critical combustion startup phase. This can waste fuel and allow excessive emissions and inefficiencies. Thus, it is desired to have an analyzer system that provides both safe startup and fault condition operation while remaining readily available.

SUMMARY

A method of operating a process combustion analyzer having a measurement cell is provided. The method includes exposing the measurement cell to exhaust of a combustion process where fuel and oxygen are combined in a burner to produce a flame. The measurement cell is heated to a temperature above the flashpoint of the fuel. When an exception or a fault condition is detected, gas is directed to the measurement cell to form a gaseous barrier between the measurement cell and unburned fuel while the condition exists. Once the condition abates, the gas flow is disengaged and process combustion gas measurements are provided.

DETAILED DESCRIPTION OF ILLUSTRATIVE EMBODIMENTS

Embodiments of the present invention generally provide a gaseous barrier between a heated process analytic sensor and a potentially flammable or deleterious environment. Embodiments of the present invention will generally be described with respect to an in situ process analytic oxygen analyzer, but embodiments of the present invention are applicable to any process analytic sensor that operates at a temperature that can potentially generate an unintended flashpoint for flammable or explosive materials. Advantageously, embodiments of the present invention may allow legacy process analytic hardware to operate in a new manner that reduces or minimizes the potential for unintended ignition while also providing the benefits of substantially immediate process analytic measurements once a combustion process is initiated.

Figure 1:
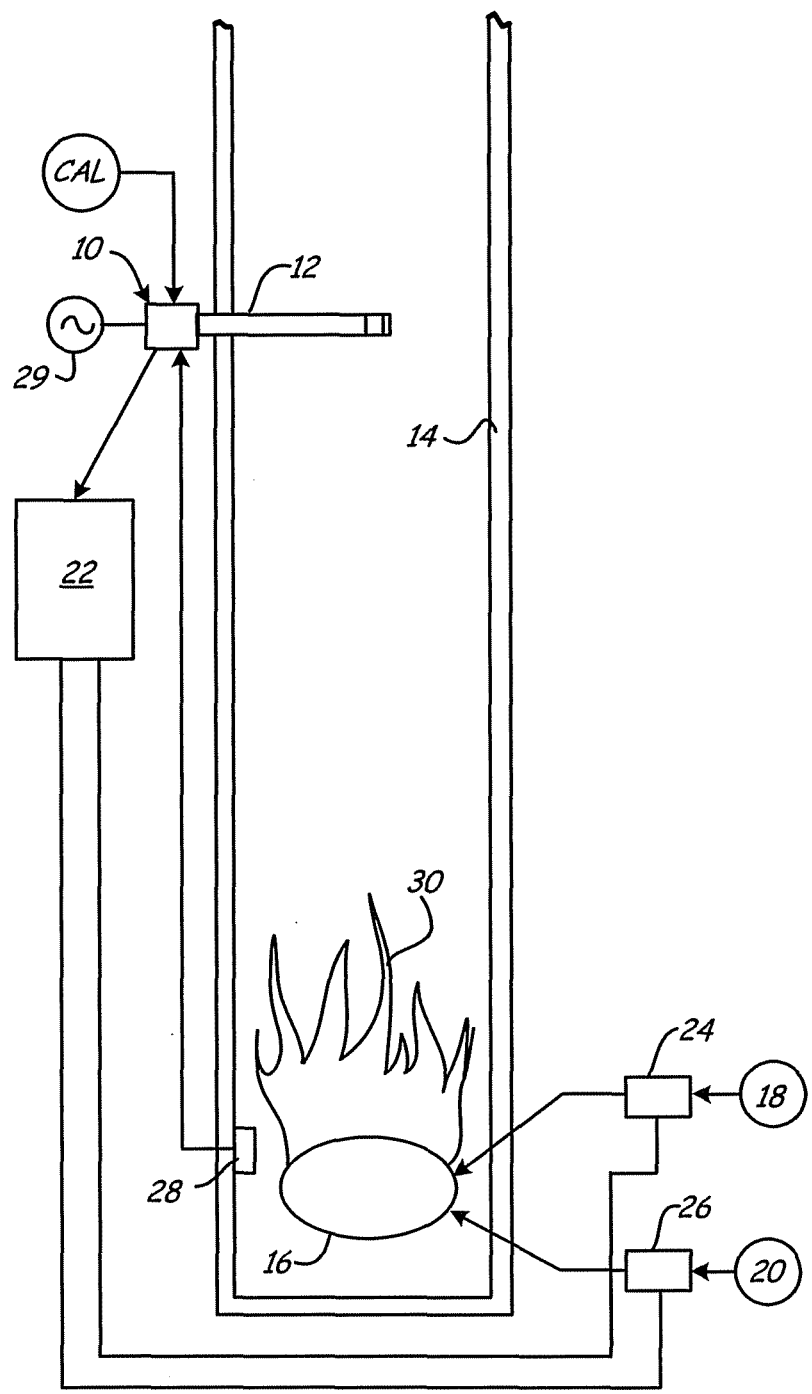
FIG. 1 is a diagrammatic view of an in situ combustion process analyzer with which embodiments of the present invention are particularly useful.

FIG. 1 is a diagrammatic view of an in situ process combustion analyzer in accordance with the prior art. Transmitter 10 can be any suitable analyzer including the X-Stream $O_2$ Combustion Flue Gas Transmitter listed above. Transmitter 10 includes a probe assembly 12 that is disposed within a stack or flue 14 and measures at least one parameter related to combustion occurring at burner 16. Typically, transmitter 10 is an oxygen transmitter, but can be any device that measures any suitable parameter related to the combustion process. Burner 16 is operably coupled to a source of air or oxygen 18 and a source 20 of combustible fuel. Each of sources 18 and 20 is preferably coupled to burner through a valve of some sort to deliver a controlled amount of oxygen and/or fuel to burner 16 in order to control the combustion process. Transmitter 10 measures the amount of oxygen in the combustion exhaust flow and provides an indication of the oxygen level to combustion controller 22. Controller 22 controls one or both of valves 24, 26 to provide closed-loop combustion control. Transmitter 10 includes an oxygen sensor that typically employs a zirconia oxide sensor substrate to provide an electrical signal indicative of oxygen concentration, content or percentage in the exhaust. Zirconia oxide sensors operate at a temperature of about 700° Celsius and thus transmitter 10 includes, within probe assembly 12, an electrical heater that is operably coupled to AC power source 29. AC power source 29 can be a 110 or 220 VAC source that provides electrical energy to one or more electrical heating elements within probe assembly 12 to heat the zirconia oxide sensor substrate to a suitable temperature.

As can be appreciated, should burner 16 experience a flameout condition, it is possible that raw fuel and air could continue to flow from sources 20, 18, respectively, which materials could contact the hot zirconia oxide sensor, which could provide an unintended source of ignition. In order to address flameout conditions, prior art methods (including that illustrated in FIG. 1) generally include a flame scanner 28 disposed to provide a signal indicative of the presence of flame 30 at burner 16. This flame scanner signal has been provided allow suitable reaction to the flameout condition. In the past, the flame scanner signal has been used to close a fuel valve and/or remove power from the analyzer thereby de-energizing the heater within probe assembly 12. In many cases, this removal of power allows rapid cooling of the zirconia oxide sensor to a temperature that is below the fuel ignition temperature, thereby creating a safe condition. However, upon restoration of flame 30 at burner 16, the analyzer heater power is restored but transmitter 10 is unavailable to provide combustion oxygen information until operating temperature of the zirconia oxide sensor is reached. This lag to reach operating temperature is typically on the order of 10-45 minutes during which the critical combustion startup phase may be wasting fuel and/or allowing excessive emissions and inefficiency.

Figure 2:
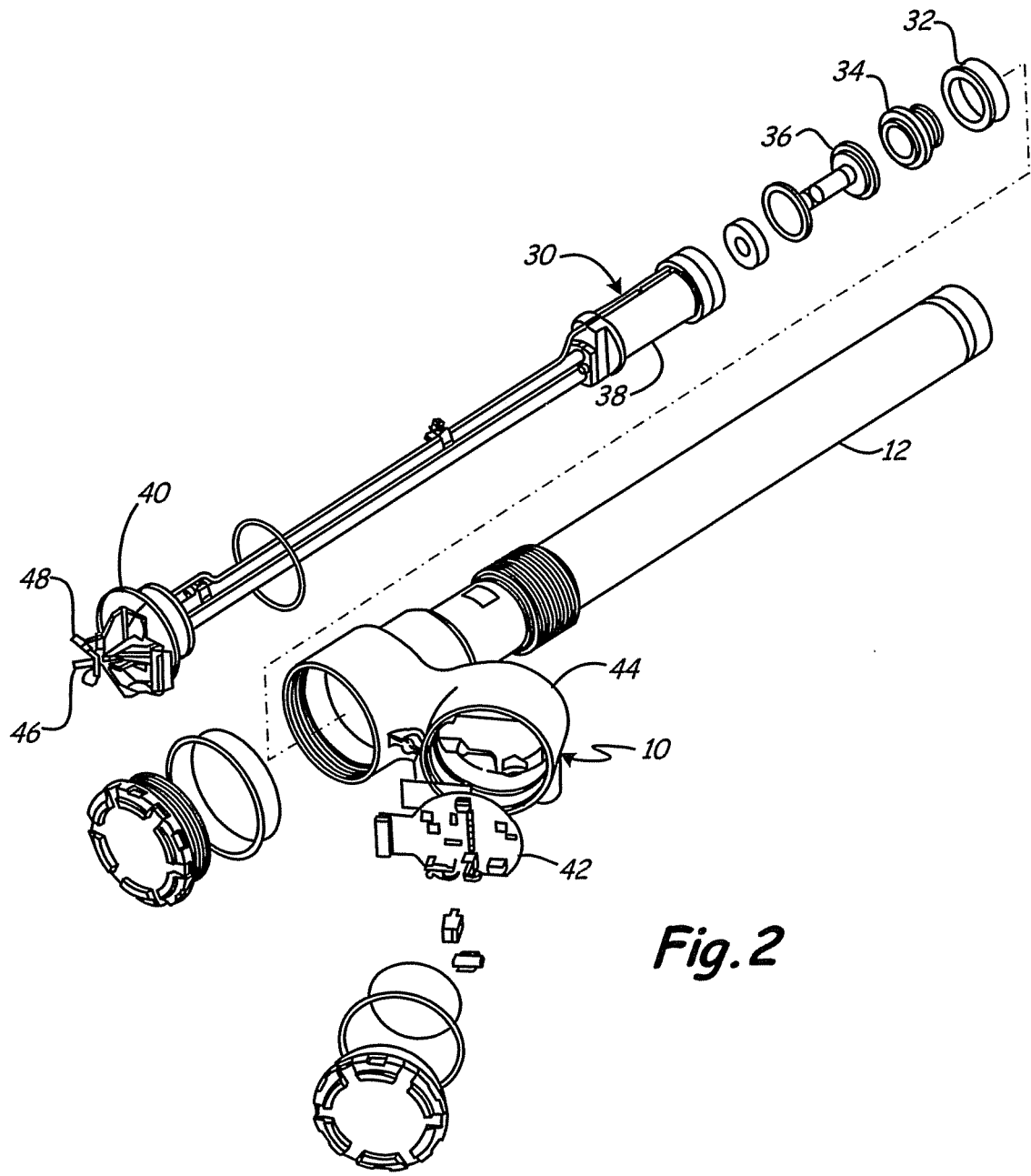
FIG. 2 is a diagrammatic exploded view of a process analytic oxygen sensor useful in accordance with embodiments of the present invention.

FIG. 2 is a diagrammatic view of an in situ process combustion analyzer with which embodiments of the present invention are particularly useful. Probe assembly 12 is generally configured to house sensor core assembly 30 which includes diffuser 32 disposed proximate metal retainer 34, which is disposed next to measurement cell 36. As described above, measurement cell 36 is operable at an elevated temperature and the elevated temperature is provided by electrical heater 38. Measurement cell 36 and heater 38 are electrically coupled to transmitter 10 via board 40. Board 40 is configured to engage electronics board 42 in housing 44. Board 40 also includes a plurality of gas inlets 46 and 48 to receive reference air and calibration gas, respectively.

Zirconia oxide sensing technology has historically measured process oxygen by using ambient or instrument air as a reference (20.95% oxygen). Periodically, the sensor may need to be calibrated where a precisely controlled amount of oxygen can be introduced to the sensor and exposed to measurement cell 36. Accordingly, ports 46 and 48 are coupled to conduits that direct the reference and calibration gases to cell 36. The reference gas is provided to a side of the zirconia oxide substrate that is away from the process gas. During calibration, however, calibration gas is supplied to the side of the zirconia substrate that is opposed to the side exposed to reference gas. In this manner, each side is exposed to a gas.

Embodiments of the present invention generally employ any non-combustible gas, typically reference air or calibration gas, as a purge gas during a flameout condition to provide a continuously flowing gas barrier between measurement cell 36 and diffuser 32. In this manner, combustible, explosive, or otherwise deleterious materials that may be accumulating within the flue are kept safely away from the hot (a temperature that is at or above the flashpoint of the combustible or explosive material) surfaces.

Figure 3:
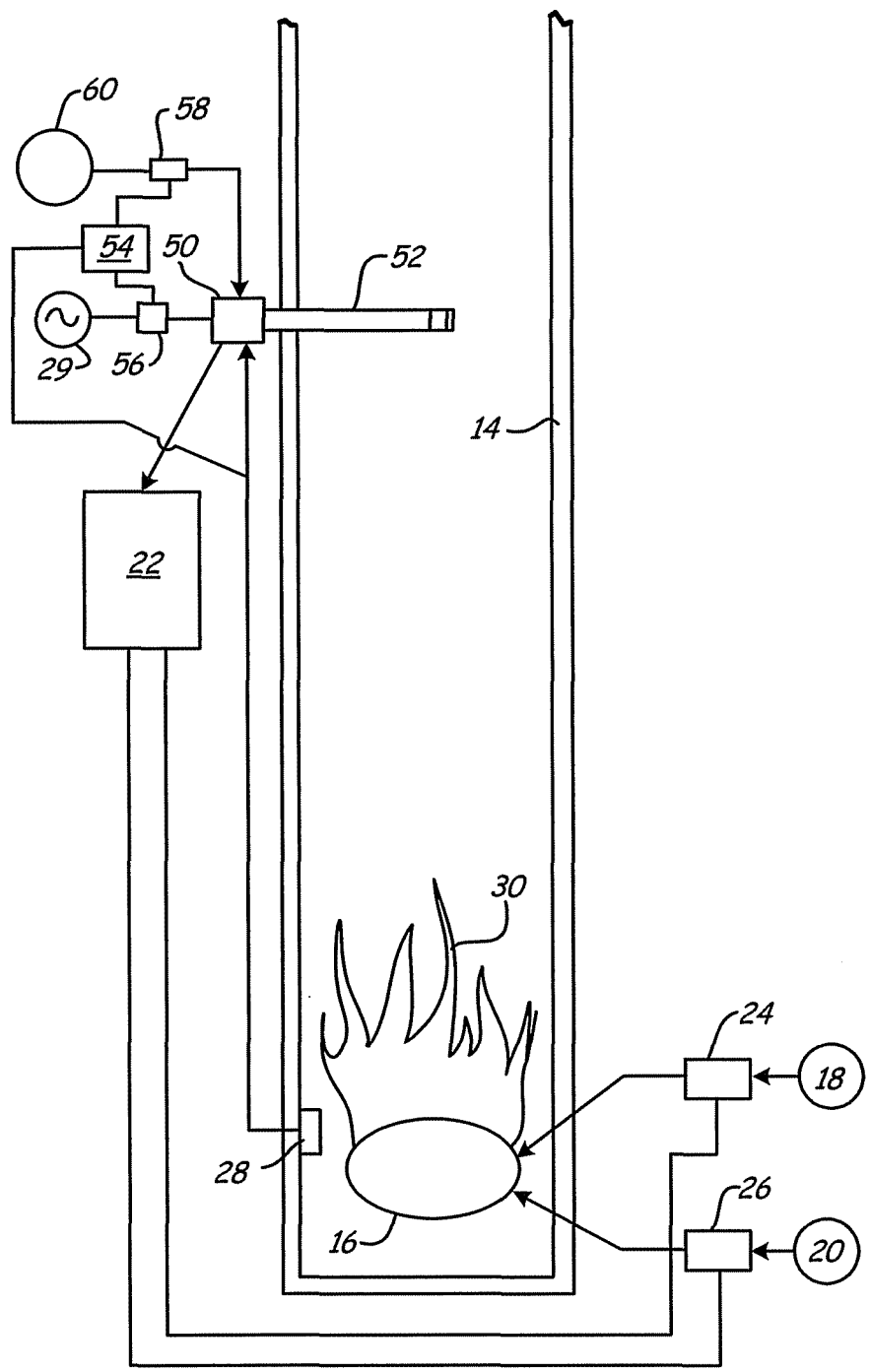
FIG. 3 is a diagrammatic view of an in situ combustion process analyzer in accordance with an embodiment of the present invention.

FIG. 3 is a diagrammatic view of an in situ combustion process analyzer in accordance with an embodiment of the present invention. Transmitter 50 includes probe assembly 52 containing therein a process gas sensor that operates at a temperature that is high enough to ignite unburned fuel from source 20 in the presence of air or oxygen from source 18 if flame 30 is lost. As shown in FIG. 3, the signal from flame scanner 28, or some other robust digital input, is coupled to a relay or switch within safety system 54. Safety system 54 can be integral with or separate from transmitter 50. Further, in embodiments where transmitter 50 is separate from safety system 54, transmitter 50 can be physically remote from system 54.

Safety system 54 is operably coupled to switch 56 to selectively couple transmitter 50 to heater power source 29. Additionally, safety system 54 is also operably coupled to pneumatic valve 58 to selectively couple source 60 to transmitter 50. Accordingly, once flame scanner reports, or otherwise indicates a flameout condition, safety system 50 can operate valve 58 to direct reference or purge gas between the measurement cell and the diffuser. In fact it is preferred that valve 58 have a non-energized state that is normally open such that safety system 54 must energize valve 58 to cease calibration gas flow. While it is preferred that air or calibration gas be used, any suitable non-flammable purge gas can be used. Moreover, a pump can be employed to direct any suitable purge gas, including air, into the calibration gas port. Those skilled in the art will appreciate that safety system 54 resembles existing automatic calibration modules, and in fact some module may be able to be programmed, or otherwise configured, such that a flameout signal will automatically engage calibration gas. Further still, those skilled in the art will recognize that the various valves and signal processing circuits of safety system 54 could be embodied wholly within an in situ process gas analyzer in accordance with embodiments of the present invention. Thus, in embodiments where transmitter 50 includes a suitable valve coupled to the calibration gas inlet, transmitter 50 itself may receive an indication of a flameout condition and engage the calibration gas valve to direct calibration gas to the measurement cell to isolate the measurement cell from potentially combustible or explosive materials.

It is believed that embodiments of the present invention can be practiced with legacy in situ combustion transmitters already deployed. Further still, the automatic generation of a flowing gaseous barrier between the thermally elevated sensor measurement cell can be useful to protect the cell from contact with other materials, such as potentially corrosive or damaging materials. While embodiments of the present invention are believed to provide significant safety and usability advantages, embodiments of the present invention can still be used with a typical flame arrestor.

Embodiments of the present invention generally utilize an electro-pneumatic system (either disposed within a transmitter or externally thereto) to introduce purge gas into a calibration port in response to an electrical signal that is responsive to burner flame status or a suitable manual selection signal. The gas flow purges the volume in front of the measurement cell and precludes entry of materials, such as flammable gas, to the high-temperature potential source of ignition (measurement cell 36). Under normal operation a purge gas valve is energized and precludes calibration gas flow. In the event that the safety system, e.g. 54, input is switched, power is removed from the valve and the ensuing air flow precludes process gas (fuel) from reaching the heated zone within seconds. This behavior facilitates safe operation while maintaining the operating temperature, thus providing a standby, hot startup capability with an emergency safe mode without removing heater power. It is anticipated that this system can also be used to optionally de-energize the heater in parallel with the safety purge. Moreover, it is contemplated that heater control can also be specifically selected to allow the measurement cell to cool to a temperature that is suitably below a flashpoint of the process gas. Once such temperature is confirmed, the reference and/or calibration gas flow could be reduced. Thus, in such a hybrid embodiment, not only is the measurement cell at a temperature that is below the flashpoint but some flowing gaseous barrier is also employed.

Figure 4A:
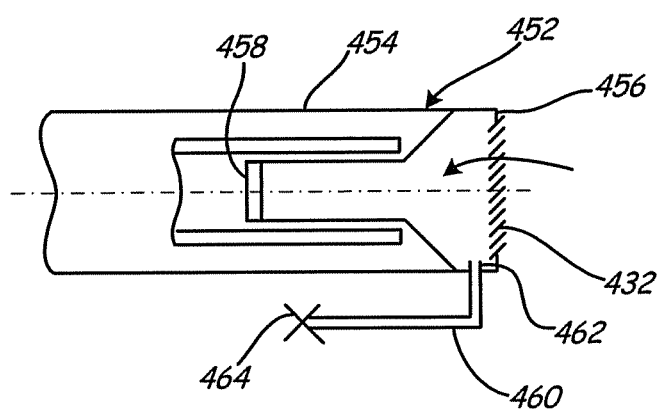
FIG. 4a is a diagrammatic view of a portion of a probe assembly operating during a normal condition.

FIG. 4a is a diagrammatic view of a distal portion of a probe assembly 452. Portion 454 includes distal end 456 which houses diffuser 432. During normal operation, as illustrated in FIG. 4a, process combustion gas diffuses through diffuser 432 and contacts sensor 458. A calibration gas conduit 460 is coupled to a calibration gas outlet 462 that is disposed between sensor 458 and diffuser 432. During normal operation, no calibration gas flows through conduit 460 as illustrated at X 464.

Figure 4B:
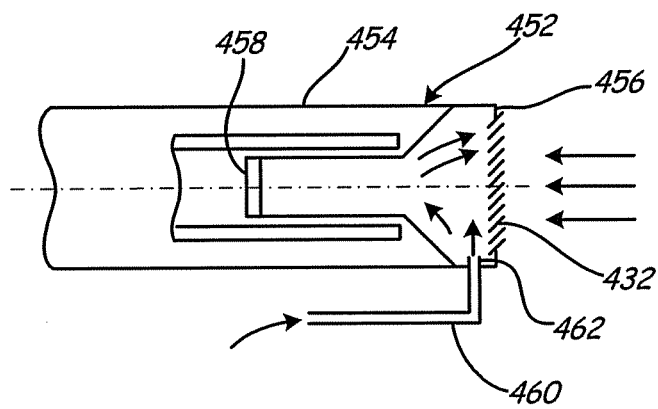
FIG. 4b is a diagrammatic view of a portion of a probe assembly during calibration.

FIG. 4b is a diagrammatic view of probe assembly 452 during a calibration. During calibration, a calibration gas is provided through conduit 460, which enters probe assembly 432 at port 462. The calibration gas flow fills the region between sensor 458 and diffuser 432. By virtue of its known constituents, measurements obtained by sensor 458 when calibration gas is proximate sensor 458 allows for errors to be detected and compensated. Embodiments of the present invention generally take advantage of the positioning of outlet 462 to provide a non-flammable gas such as reference air, calibration gas, or any other suitable gas, when an unsafe condition (such as a flameout or manual standby condition) is detected.

Figure 5:
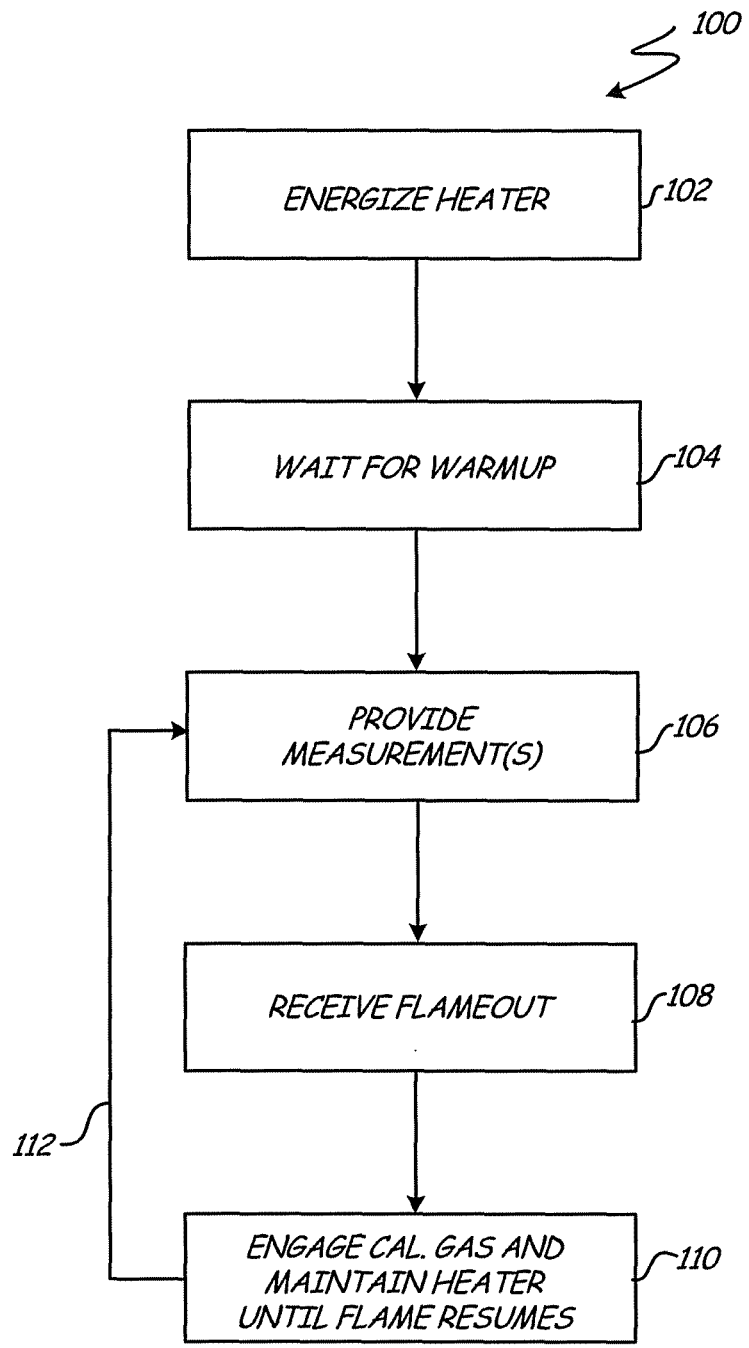
FIG. 5 is a flow diagram of a method of operating an in situ combustion process analyzer in accordance with embodiments of the present invention.

FIG. 5 is a flow diagram of a method of operating an in situ process combustion analyzer in accordance with embodiments of the present invention. Method 100 begins at block 102 where a heater of the analyzer is engaged to warm a process analytic gas sensor, such as a process analytic oxygen sensor, to an operating temperature. As set forth above, an operating temperature for typical zirconia oxide oxygen sensors is approximately 700° Celsius. Method 100 continues at block 104 where the analyzer waits until the operating temperature has been reached. Once the operating temperature has been reached, control passes to block 106 where the process analyzer begins providing process gas measurements, such as process oxygen levels. At block 108, a flameout indication is received. This flameout indication can be received by an in situ process oxygen analyzer, a device external to the process oxygen analyzer, or both. Regardless, once the flameout indication is received, control passes to block 110 where a source of calibration gas is engaged to generate a gaseous barrier between the thermally-elevated measurement cell and any materials near the diffuser. Such materials can include flammable or potentially explosive process gas, but may also include any material that may have deleterious effects on the measurement cell. The gas flow can be engaged by the transmitter itself and/or an external device upon reception of the flameout indication. While in block 110, the measurement cell of the process gas analyzer is preferably maintained at an elevated temperature, at least, and preferably at the full operating temperature. Method 100 remains in the status of block 110 until the flameout condition abates, at which time control returns to block 106 along line 112 and the analyzer begins providing measurements. However, in embodiments where the thermal control system of the probe has allowed the measurement cell to cool to a temperature that is below the operating temperature, control returns to block 102, where the heater is energized to heat the measurement cell to the operating temperature.

Although the present invention has been described with reference to preferred embodiments, workers skilled in the art will recognize that changes may be made in form and detail without departing from the spirit and scope of the invention.

What is claimed is:

1. A method of operating a process combustion analyzer having a measurement cell, the method comprising:
   exposing the measurement cell to exhaust that has diffused through a diffuser, the exhaust being of a combustion process wherein fuel and oxygen are combined in a burner to produce a flame;
   heating the measurement cell to a temperature above a flashpoint of the fuel;
   detecting a flameout condition and directing a purge gas to the measurement cell to form a gaseous barrier between the measurement cell and unburned fuel while the flameout condition exists and reducing heater power during the flameout condition;
   upon loss of the flameout condition, disengaging the purge gas flow, restoring heater power and providing process combustion gas measurements; and
   wherein process gas measurements are provided substantially immediately after loss of the flameout condition.

2. The method of claim 1, wherein heating the measurement cell is done with a heating element disposed proximate the measurement cell in a probe assembly.

3. The method of claim 2, wherein the probe assembly is disposed in a flue.

4. The method of claim 1, wherein the process gas measurements are process oxygen measurements, and the temperature is 700 degrees Celsius.

* * * * *